United States Patent [19]

Stewart

[11] Patent Number: 5,007,421

[45] Date of Patent: Apr. 16, 1991

[54] BREATHING APPARATUS

[76] Inventor: John S. S. Stewart, 74 The Common, Parbold, Wigan, Lancashire WN8 7EA, England

[21] Appl. No.: 67,785

[22] PCT Filed: Sep. 30, 1986

[86] PCT No.: PCT/GB86/00581

§ 371 Date: Jul. 28, 1987

§ 102(e) Date: Jul. 28, 1987

[87] PCT Pub. No.: WO87/01949

PCT Pub. Date: Apr. 9, 1987

[30] Foreign Application Priority Data

Oct. 1, 1985 [GB] United Kingdom ................. 8524181

[51] Int. Cl.[5] ............................................. A61M 16/00

[52] U.S. Cl. ....................... 128/204.180; 128/205.250; 128/205.280

[58] Field of Search ....................... 128/200.24, 200.29, 128/201.27, 201.28, 204.18, 205.13, 205.24, 205.25, 205.26, 205.28

[56] References Cited

U.S. PATENT DOCUMENTS

| | | | |
|---|---|---|---|
| 3,366,108 | 1/1968 | Blackburn et al. | 128/205.24 |
| 4,440,164 | 4/1984 | Werjefelt | 128/205.25 |
| 4,559,939 | 12/1985 | Levine et al. | 128/201.28 |

FOREIGN PATENT DOCUMENTS

| | | |
|---|---|---|
| WO86/03171 | 6/1986 | PCT Int'l Appl. . |
| WO86/05461 | 9/1986 | PCT Int'l Appl. . |
| 426962 | 4/1935 | United Kingdom . |
| 789466 | 1/1958 | United Kingdom . |
| 862984 | 3/1961 | United Kingdom . |
| 944932 | 12/1963 | United Kingdom . |
| 1494168 | 12/1977 | United Kingdom . |
| 2045090 | 10/1980 | United Kingdom . |
| 2150838A | 7/1985 | United Kingdom . |
| 2169209A | 7/1986 | United Kingdom . |

OTHER PUBLICATIONS

Preliminary Examination Report PCT/GB 86/00581, 1/87.

International Search Report PCT/GB 86/00581, 11/87.

*Primary Examiner*—Lee S. Cohen
*Assistant Examiner*—J. P. Lacyk
*Attorney, Agent, or Firm*—Bacon & Thomas

[57] ABSTRACT

Breathing apparatus for aircraft passengers and others comprising:

(a) means (1) for supplying respiratory gases to a user, said supply means being detachably connectable to a first respiratory gas source (3), and thereby constituting a first oxygen supply system, said supply means including valve means (2), which valve means, when said supply means (1) is detached from the first respiratory gas source (3), automatically closes and prevents admission of noxious or hot gases into said supply means (1), (b) means for supplying (5) or enabling supply (50) of a second respiratory gas source to said supply means (1), and constituting a second oxygen supply system, in which an absorption means (4) for absorbing carbon dioxide is included; and either (c) means (6A) for automatically switching from said first oxygen supply system to said second oxygen supply system when said supply means (1) is detached from said first respiratory gas source (3); or (c') means (6) for manually or automatically causing said second oxygen supply system to become operative to supplement or replace said first oxygen supply system, said second oxygen supply system continuing to be operable when said supply means (1) is detached from said first respiratory gas source (3).

26 Claims, 8 Drawing Sheets

BREATHING APPARATUS

BACKGROUND OF THE INVENTION

This invention relates to breathing apparatus, particularly for aircraft passengers.

In some aircraft accidents lives are lost due to the consequences of fire and in particular to the inhalation of smoke and fumes or hot gases. In some accidents passengers are overcome while still seated but do not show evidence of severe external burns. Some of these passengers could perhaps have been saved if a portable respirator, so called gas mask, had been available for each. Such devices can remove smoke and noxious gases by filtration and absorption. However, inhalation of very hot air, in the absence of noxious gases, can still cause death from thermal damage to the internal lining of the lungs. The use of a conventional gas mask would afford little or no protection against such very hot air. Furthermore in an aircraft fire noxious fumes from fuel and other sources may be present in such large amounts that normal filtration or absorption facilities can become blocked or exhausted. Additionally the fierce combustion of aircraft fuel can substantially reduce the oxygen content of the cabin atmosphere. In pathophysiological terms alveolar burns, pulmonary oedema and shock may contribute to acute anoxia which may be of anoxic, anaemic, stagnant or histotoxic type or to a combination of some or all of these. Lives might also have been saved if each passenger had a portable respirator with self contained compressed air cylinder, as used by firemen and subaqua divers, but such apparatus is not practicable because of cost, weight and a high degree of skill and training required to use it.

There are three main types of self contained breathing apparatus for aircraft passengers: firstly those which have filters to remove smoke and noxious gases, but these do not protect against hot gases; secondly those which provide a continuous supply of air or oxygen from a pressurised cylinder, but large volumes of gas are required and cylinders are heavy; and thirdly those which use pure oxygen in a rebreathing system with carbon dioxide absorber, but measures must be taken to maintain the absorbent material in good condition until it is needed and to remove nitrogen from the system.

The efficiency of the absorbent material is dependent upon many chemical, physical and other factors. Importantly, the material deteriorates and becomes exhausted if it is exposed to air but frequent replacement is very expensive in maintenance costs. The activity is preserved for many months if the absorbent is sealed to prevent contact with air, which contains carbon dioxide and water vapour, but this is not easy to do. There is a substantial amount of space between absorbent granules and this space is filled with air. If both ends of the container are sealed, the pressure within varies as the aircraft ascends and descends. This fluctuation may rupture the seal, even when there is a minimal volume of retained air.

It is dangerous to rebreath air in the presence of an absorber, for acute anoxia may occur without warning, but pure oxygen is safe. Nitrogen should therefore be reduced but this should be achieved without waste of oxygen. The apparatus will be used by passengers without training or experience and with very little instruction. Thus the system should be simple to use and where possible automatic. It may also have the oxygen source fixed to the conveyance means and may deliver oxygen to the reservoir. To reduce the risk of pure oxygen exacerbating a fire, an oxygen-rich atmosphere may be used rather than a pure oxygen atmosphere. If nitrogen wash out is not complete, the system is safe to use when the oxygen inflow is equal to or in excess of oxygen usage. If oxygen usage is in excess, then time is limited by the amount of oxygen remaining.

A harness with adjustable straps may be used to retain a face mask in position and obtain a good fit to prevent gas leaks. Provision must also be made for children and for infants.

SUMMARY OF THE INVENTION

It is an object of the present invention to at least minimize all the problems, including those which are peculiar in nature and intensity to aircraft fires, by the use of a simple, relatively inexpensive, portable breathing equipment.

There are three main situations which can exist in an aircraft and which require safety means to operate. These are:

(1) Decompression (2) An in-flight fire (3) Escape of passengers from the aircraft on landing.

Face masks connected to an oxygen supply are already provided in aircraft in case of sudden decompression at altitude. The user is supplied with a source of pure oxygen until the decompression problem has been solved. In the case of situations (2) and/or (3) an additional respiratory gas source is required which is independent of the oxygen supply already provided in aircraft. This additional respiratory gas source can be used to supplement the existing oxygen source in aircraft during an in-flight fire and/or the additional gas source can be utilised independently when escape from the aircraft on landing is necessary.

Thus, the breathing apparatus of the present invention can be utilised for situations (1) and/or (2) and/or (3) referred to above. Accordingly, in one aspect of the present invention, the breathing apparatus can be utilised to automatically switch from a first oxygen supply system to a second oxygen supply system, when supply of oxygen from said first supply system is terminated. In further aspect of the present invention, said second oxygen supply system can be brought in to supplement the first oxygen supply system and thereafter the second system can itself continue to operate as a second system when supply of oxygen from the first system is terminated.

According to the present invention there is provided breathing apparatus for aircraft passengers and others comprising:

(a) means for supplying respiratory gases to a user, said supply means being detachably connectable to a first respiratory gas source, and thereby constituting a first oxygen supply system, said supply means including valve means, which valve means, when said supply means is detached from the first respiratory gas source, automatically closes and prevents admission of noxious or hot gases into said supply means, (b) means for supplying or enabling supply of a second respiratory gas source to said supply means, and constituting a second oxygen supply system, in which an absorption means for absorbing carbon dioxide is included; and either (c) means for automatically switching from said first oxygen supply system to said second oxygen supply system when said supply means is detached from said first respiratory gas source; or (c') means for manually or automatically causing said second oxygen supply system to become operative to supplement or replace said first oxygen supply system, said second oxygen supply system continuing to be operable when said supply means is detached from said first respiratory gas source.

Preferably, said means for supplying respiratory gases to a user includes means for covering the respiratory apertures of the user selected from a partial face mask, a complete face mask, a hood or a bag.

In an embodiment of the invention, the means for enabling supply of a second respiratory gas source to said supply means comprises a filter arrangement.

Desirably, the means for supplying a second respiratory gas source to said supply means comprises a reservoir for containing respiratory gases and/or expired gases, so that said apparatus includes a rebreathing system and functions as a respirator or ventilator.

Further preferably, said automatic switching means includes a release mechanism for rendering said absorption means operative when said supply means is detached from said first respiratory gas source. Alternatively, said automatic switching means comprises a seal/obturator means which renders the absorption means operative when the supply means is detached from said first respiratory gas source.

The apparatus of the invention may include one or more of the following:

a heat sink;

an additional respiratory gas source;

an additional $CO_2$ absorber;

an additional filter;

an additional reservoir;

an additional release means; and an additional valve or valves.

The reservoir may be enlarged to make a combined mother and young child unit.

The apparatus of the invention may also include a logic circuit for controlling automatic delivery of apparatus, selection and supply of respiratory gases, broadcasting of instructions to passengers and providing an indication if apparatus has been tampered with or opened.

According to an embodiment of the present invention there is provided breathing apparatus comprising a face mask attached to but detachable from an oxygen supply tube and connected to an inflatable reservoir or bag held in a deflated rolled up condition but releasable to provide when attached and deflated, an oxygen supply system and, when detached and inflated a portable respirator or ventilator in a closed rebreathing system with rebreathing bag and oxygen supply in a microclimate free from noxious or hot gases.

The functions of the component parts of such apparatus are as follows:

The face mask covers the nose and mouth, and may be extended to cover the eyes, and fits onto the face to provide a seal to prevent inward movement of noxious or hot gases whilst allowing outward movement of the exhaust gases when the rebreathing bag is rolled up.

The self closing valve when held open by the oxygen supply tube allows the passage of gases in both directions within the tube. When the oxygen supply tube is removed the valve is closed and does not allow the passage of gases in either direction.

The carbon dioxide absorber absorbs carbon dioxide from the expired air.

The reservoir may be rolled up and retained thus by a retain/release mechanism in one position or it may be freed and able to be inflated when the retain/release mechanism is in another position. When the reservoir bag is rolled up the equipment behaves as a simple oxygen delivery system. When the bag is released the equipment behaves as a closed rebreathing system.

The retain/release mechanism may be used to retain the bag in a rolled up position or to release it from this position to allow it to be inflated either from the oxygen supply or with expired air. The guide means attached to the oxygen supply tube ensures that pulling the release mechanism first releases the bag reservoir. The mechanism is also designed to ensure that the bag is automatically released when the mask is disconnected from the oxygen supply.

In practice, during an emergency face masks would be automatically delivered to all passengers, as presently happens on sudden cabin decompression. Each passenger puts a face mask in place and inhales oxygen through the oxygen supply tube. Exhaled air is voided to the cabin atmosphere and the lungs become filled with oxygen or oxygen enriched air. Thus the partial pressure of oxygen in the lungs is increased. This breathing of oxygen may be continued if necessary at normal atmospheric pressure for fifteen minutes or longer without side effects. When the passenger has to leave the aircraft cabin quickly a maximum inspiration is taken and the breath is held for a moment. The face mask is then supported with one hand while the oxygen supply tube is pulled out with the other and this automatically releases the rolled up reservoir. Alternatively the release mechanism may be operated sequentially, firstly to release the inflatable reservoir and to inflate it with oxygen from the oxygen supply tube and secondly after a suitable interval to detach the oxygen supply tube. In either event exhaled air then passes through the carbon dioxide absorber and inflates or further inflates the reservoir which becomes a rebreathing bag. Rebreathing could take place for several minutes without ill effect in the absence of an absorber but the presence of this extends the time for which rebreathing can take place without dangerous build up of carbon dioxide. Thus each passenger takes with him his own portable breathing apparatus with rebreathing system and oxygen supply in a microclimate at normal temperature, free from noxious or hot gases.

If a passenger is unconscious the same apparatus can be used by a member of the cabin staff to secure his safe evacuation but with slightly different use. Firstly, the face mask is placed in position and held there by hand. Secondly, the bag release is operated without disconnecting the oxygen supply. Thirdly the reservoir is inflated with oxygen from the oxygen supply. Fourthly, the oxygen supply tube is disconnected from the face mask. The unconscious passenger now has his own portable oxygen supply and rebreathing system. If necessary however, the apparatus can be used as a ventilator to inflate the lungs by manual compression of the reservoir while holding the face mask firmly in contact with the passenger's face.

This invention also relates to improvements in passenger protection breathing apparatus including a seal mechanism which is not affected by change of cabin pressure, a co-axial circuit and valve arrangement to ensure efficient elimination of nitrogen with economical use of oxygen, means for switching the carbon dioxide absorber from the closed sealed storage mode to the open unsealed breathing mode, an improved harness for donning and adjustment and a modification for protection of infants and young children. There is automatic unsealing and the apparatus may be used by unskilled and untrained persons.

The functions of the component parts of such apparatus are as follows:

The cover enables breathable gas to be carried to the respiratory apertures and carries expired gas to the carbon dioxide absorber. It may be a half mask covering nose and mouth, a full mask covering in addition eyes and face, a hood covering the head, or otherwise and it may be composed of rubber, plastic or other material.

The self closing valve when held open by the oxygen supply tube allows the passage of gases in both directions within the tube. When the oxygen supply tube is removed the valve is closed and does not allow the passage of gases in either direction.

The carbon dioxide absorber absorbs carbon dioxide from the expired air. It comprises a container, corrugated plastic tubing or otherwise, which holds absorbent material, soda lime or otherwise.

The reservoir, a rubber bag or otherwise, holds breathable gas and functions both as an expansion chamber during the storage mode and also, during the breathing mode, as an oxygen collection chamber and rebreathing bag.

The oxygen source is a source of breathing oxygen contained in a small pressure vessel, cylinder or otherwise, activated by a cord pull or other mechanism. This may be part of or attached to the release means. Additional or alternative sources may be provided from major fixed storage vessels from chemical generators or from other means. Where necessary a quick release means is provided to disconnect portable from fixed parts of the apparatus. The oxygen source is fixed to the conveyance means to prevent it from obstructing escape.

The oxygen supply and delivery means comprising tubes, plastic or otherwise, conveys oxygen from the source and delivers it to the reservoir where it may be most efficiently used. Interposed between these two tubes is part of the seal mechanism described later. To avoid separate tubes which may become entangled one is placed inside the other in a co-axial arrangement.

An exit valve spring loaded or otherwise, permits gas to escape from the cover to the exterior when pressure within the system rises above a determined amount, preset or otherwise. It must be sited in the cover close to the respiratory apertures to be most efficient.

The seal means provides in essence an effective seal at one end of the container which holds the absorbent material. The main seal, rubber or otherwise, is attached to an obturator, plastic or otherwise, and these together occlude completely the lumen of the outer case, which is made of plastic or otherwise, when the mechanism is in the closed position. This effectively seals one end of the absorber container but the other end opens into the reservoir which is a closed system not open to the air and in which the absorbent material will keep for many months. Additional seals, rubber or otherwise, are provided near to the ends of the obturator to ensure that the obturator remains parallel to the outer case. The seal nearest to the oxygen source, called the pneumatic seal, also seals the oxygen supply tube so that the obturator is automatically moved to the open position by oxygen under pressure when the oxygen supply system is activated and the mid seal between the main and pneumatic seals prevents passage of oxygen directly into the mask. An external seal is required where the obturator expansion passes through the case.

The switch on means comprises an obturator in which there is an aperture running from proximal to distal in the obturator. Movement of the obturator essentially switches the absorber from the closed storage mode to the open breathing mode. In the storage mode the obturator is close to the oxygen supply tube and the main seal is in the closed position with the obturator aperture on the absorber side of the seal. The obturator cannot move beyond this position because there is an expansion of the obturator at the other end which is prevented by the outside of the outer case from moving further. This expansion, plastic or otherwise, also serves as a handle to move the obturator manually, and to indicate its position. In the breathing mode the obturator is at the opposite end of the outer case prevented from moving further by the end wall of the case, the seal is broken and the aperture is in line with the channels to mask and absorber so that gases can pass freely to and fro. Thus the conversion means switches the absorber means from the closed storage mode, in which the absorber means is sealed and unavailable for use, to the open breathing mode in which the absorber is unsealed and available for use. Alternatively the obturator may be moved by a coiled up spring or otherwise between the expanded end of the handle and the outer side of the outer case. The spring may be held in the coiled up position by the wall of the box or container of the breathing apparatus so that it is automatically released when the apparatus is removed from the box.

Thus each passenger takes with him his own portable breathing apparatus with rebreathing system and oxygen supply in a microclimate at breathable temperature, free from noxious or hot gases. If a passenger is unconscious the same apparatus can be used by a member of the cabin staff as a ventilator to inflate the lungs by manual compression of the reservoir while holding the face mask firmly in contact with the passenger's face. Since the apparatus is for use in fire and smoke it should be resistant to chemical substances found there and to high temperature.

The donning means, comprising a strap or straps rubber or otherwise, is used to don the mask, or hood, and to adjust the fit of the mask on the face. The donning straps are held and are used to pull on the mask. The same straps are then pulled through the buckles to tighten the fit on the face but the ends may be difficult to find. This is avoided if each strap is continuous in a figure of eight loop for the strap to be tightened is the same as that used for donning.

The passenger protection breathing apparatus may be used as a hood, plastic or otherwise, with a neck seal, plastic or otherwise, for older children. In such a system the dead space is greater and relatively more oxygen will be required to flush out nitrogen.

The adult passenger protection breathing apparatus may be modified for babies and small children by attaching a large bag, plastic or otherwise instead of the reservoir. The distal end is sealed in the storage mode but has a means to facilitate tearing it open. It also has a draw string about the middle. A baby is placed completely inside the bag and the end of the bag is folded over several times and held closed with strong spring clips. Alternatively it is placed over the head and body of a small child and the draw string is pulled tight around the abdomen for closure. In the meantime the mother or other parent has donned her face mask and there is now a dual tandem system in which the mother circulates her expired gases through the absorber. Since the large rebreathing bag may initially be filled with air a larger amount of oxygen will be required to flush out nitrogen. It will be noted that the passenger has only to put on the mask, tighten the straps and breathe normally. The high pressure in the oxygen source ensures that the oxygen flow rate is considerably in excess of uptake. Thus more oxygen is entering the bag than is being removed by the lungs and there is an oxygen gradient from bag to lungs. When the bag is full, nitrogen rich gas is exhausted from the system and oxygen levels will approach 100% in a few minutes. Relevant anaesthetic principles are described in a synopsis of anaethesia by Atkinson et al 1984. Wright, Bristol. The circuit described is similar to a Magill circuit but uses coaxial flow. However this is different from the Bain and Lack circuits and involves an inventive step to meet the needs of aircraft passengers using a rebreathing system and carbon dioxide absorber while breathing spontaneously and not under anaesthesia.

Cbviously improvements and adaptation of the described system may be made for use by experienced staff and changes may be made for ease of maintenance. The oxygen supply may be controlled by a manually operated valve for nitrogen washout or otherwise and an "on demand" system may be incorporated for use during exercise. Soda lime, or other absorbent agents may be used and indicators which change colour when the agent is exhausted may be used to confirm at the time of maintenance that the absorbent is active.

BRIEF DESCRIPTION OF THE DRAWINGS

The present invention will be further illustrated, by way of example, with reference to the accompanying drawings, in which.

DESCRIPTION OF THE PREFERRED EMBODIMENTS

Figure 1:
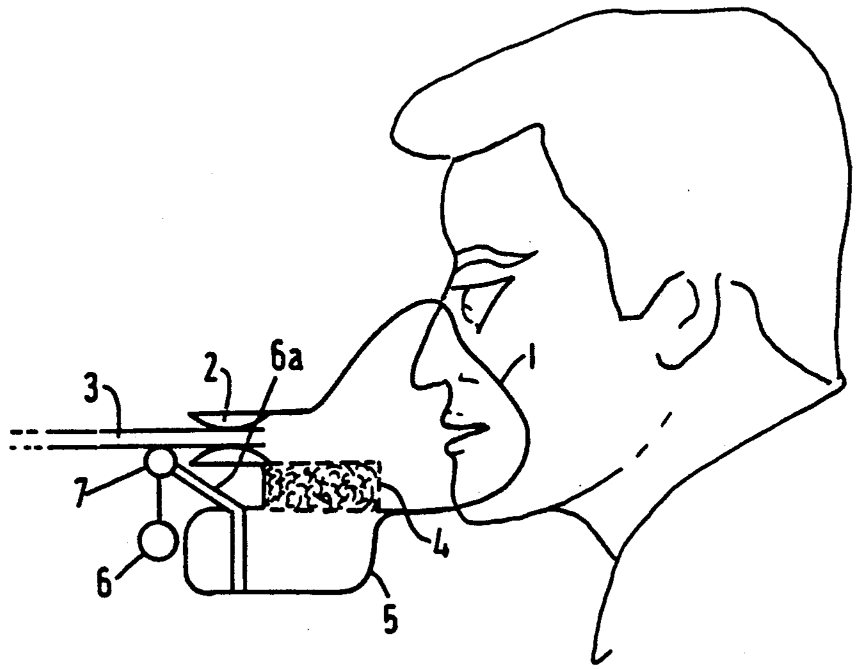
FIG. 1 shows in perspective and cross section the breathing apparatus with the oxygen supply tube attached and the reservoir retained in the deflated rolled up position by the retain/release mechanism.
Figure 2:
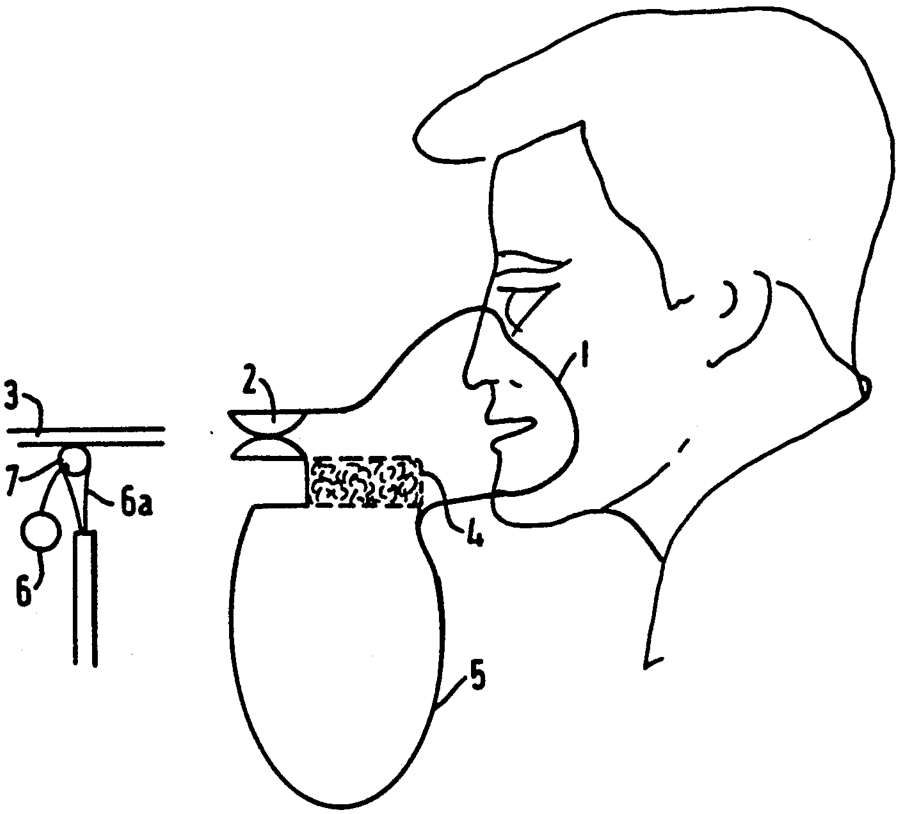
FIG. 2 shows in perspective and cross section the breathing apparatus with the oxygen supply tube detached and the reservoir released in the inflated position with the retain/release mechanism still attached to the oxygen supply tube.

As illustrated in the embodiment shown in FIGS. 1 and 2, the breathing apparatus comprises a face mask 1, made for example from plastic or rubber, connected by way of a self closing valve 2, made for example of opposing rubber flaps, to an oxygen supply tube 3, whether plastic or otherwise, and by way of a carbon dioxide absorber 4, whether chemical using soda lime or otherwise, to a rolled up reservoir 5, whether an inflatable rubber bag or otherwise, with a manual release mechanism 6, whether a single cord tied to a rubber band or otherwise, led through a guide means 7, whether a metal ring or otherwise and connected to the oxygen supply tube 3, cord 6A being connected to the reservoir 5. In FIG. 1 the breathing apparatus is shown attached to the oxygen supply tube 3, and in FIG. 2 the breathing apparatus is shown detached. In particular it should be noted in FIG. 2 that the oxygen supply tube 3 is detached, that the valve 2 is closed, that the manual release mechanism 6 and the cord 6A are still connected to the oxygen supply tube 3 but not to the reservoir 5 which is now inflated.

In order to detach the oxygen supply tube 3, the face mask 1 is held and the oxygen supply tube 3 is pulled out of the self closing valve 2. The same movement will pull the cord 6A attached to the oxygen supply tube 3 and will automatically release the rolled up reservoir 5 retained by the cord 6A of the release mechanism 6. If desired, the rolled up reservoir 5 can be released for inflation with oxygen via the oxygen supply tube 3 and via the carbon dioxide absorber 4 by manually pulling the release mechanism 6 through the guide means 7 away from the rolled up reservoir 5 without pulling the oxygen supply tube 3 out of the self closing valve 2.

Whilst a face mask has been utilised in FIGS. 1 and 2 to envelope the respiratory apertures, it is also possible to envelope the whole head or body utilising for example, a bag or hood. Clearly it would be advantageous if the material used to envelope the respiratory apertures or indeed the entire apparatus is fire resistant. The volume of the envelope should be large enough for normal breathing when used as an oxygen supply system and might itself be expansible and contractible as is a bag or hood.

Figure 3:
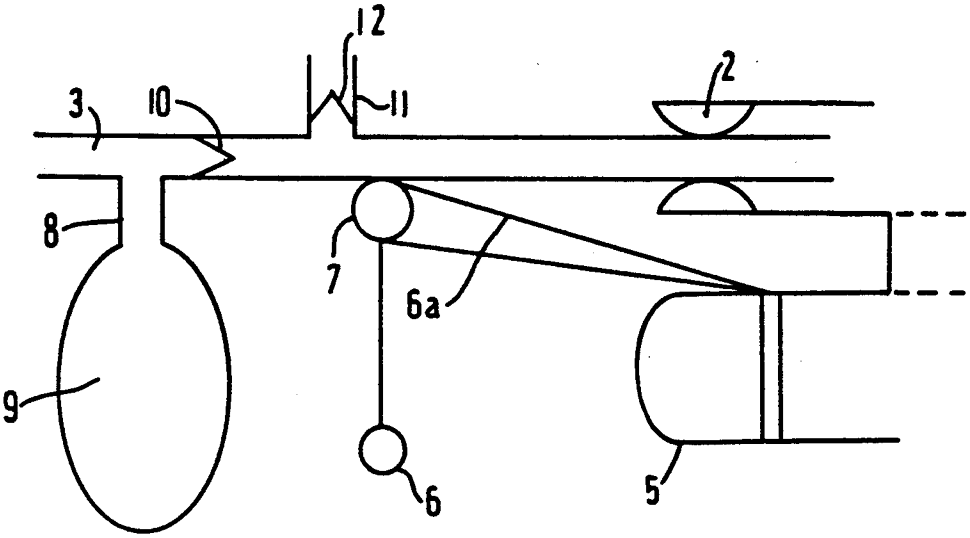
FIG. 3 schematically shows the inclusion of an additional reservoir to compensate for the intermittent nature of breathing of a user.

Whilst the flow of oxygen through tube 3 is constant, respiratory breathing is of an intermittent flow nature. Accordingly to compensate for such situation as shown in FIG. 3, an additional reservoir 9 can be added and could for example be placed adjacent to the mask and connected by a side arm 8 to the oxygen supply tube 3. A one way valve 10 between the side arm and the mask would prevent rebreathing into bag 9. Expired air passes along side arm 11 and is vented to the exterior through an additional one way valve 12.

The supply tube 3 is connected to a supply source of respiratory gases comprising oxygen either as pure oxygen or air. The choice of gas would be made by the aircrew or cabin staff. The oxygen might be generated chemically or stored under pressure in containers designed for the purpose and with suitable pressure regulation means associated therewith. Such a supply source might serve a plurality of outlets. Air might be similarly stored or obtained from another source free from noxious or hot gases. The valve 2 may be a simple valve to allow free passage of respiratory gases when open and to allow no passage of gases in either direction when closed. However, this or another more complex valve might be used to regulate the gas flow with reduction from source pressure to delivery pressure. The supply tube might be reconnectable as well as disconnectable. Reconnection may be achieved for example simply by pushing the supply tube 3 through the valve 2, for example a valve made from opposed flaps of rubber or otherwise thick at the base and thin at the free edge to preserve the ability to direct flow.

Whilst valve 2, when closed, prevents admission of noxious or hot gases into said supply means it can operate as an exit valve by removal of the second element of the valve to permit escape of expired air into the atmosphere.

The absorber 4 and reservoir 5 are excluded from the breathing circuit when used as an oxygen supply system but both are included in the circuit when used as a portable respirator or ventilator. In the embodiment using a hood or a bag, there is an enlarged cover 1. In a hood, respiratory action would probably be sufficient to circulate expired air but if not, as in the bag for an infant, a manually operated bellows could be used.

Figure 4:
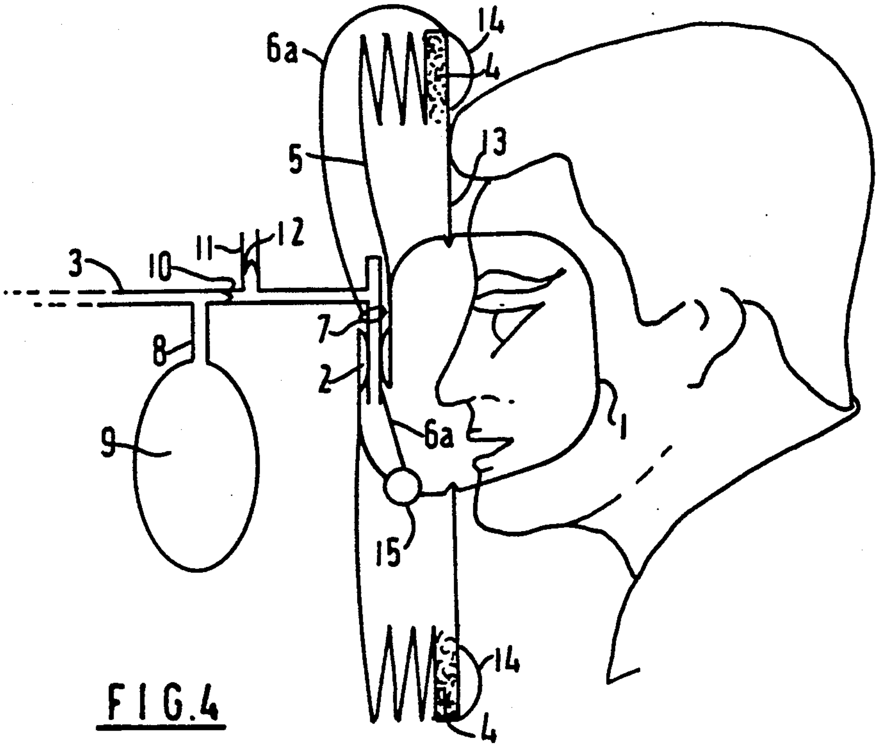
FIG. 4 schematically shows the use of a combined face mask and hood arrangement in the inoperative position.
Figure 5:
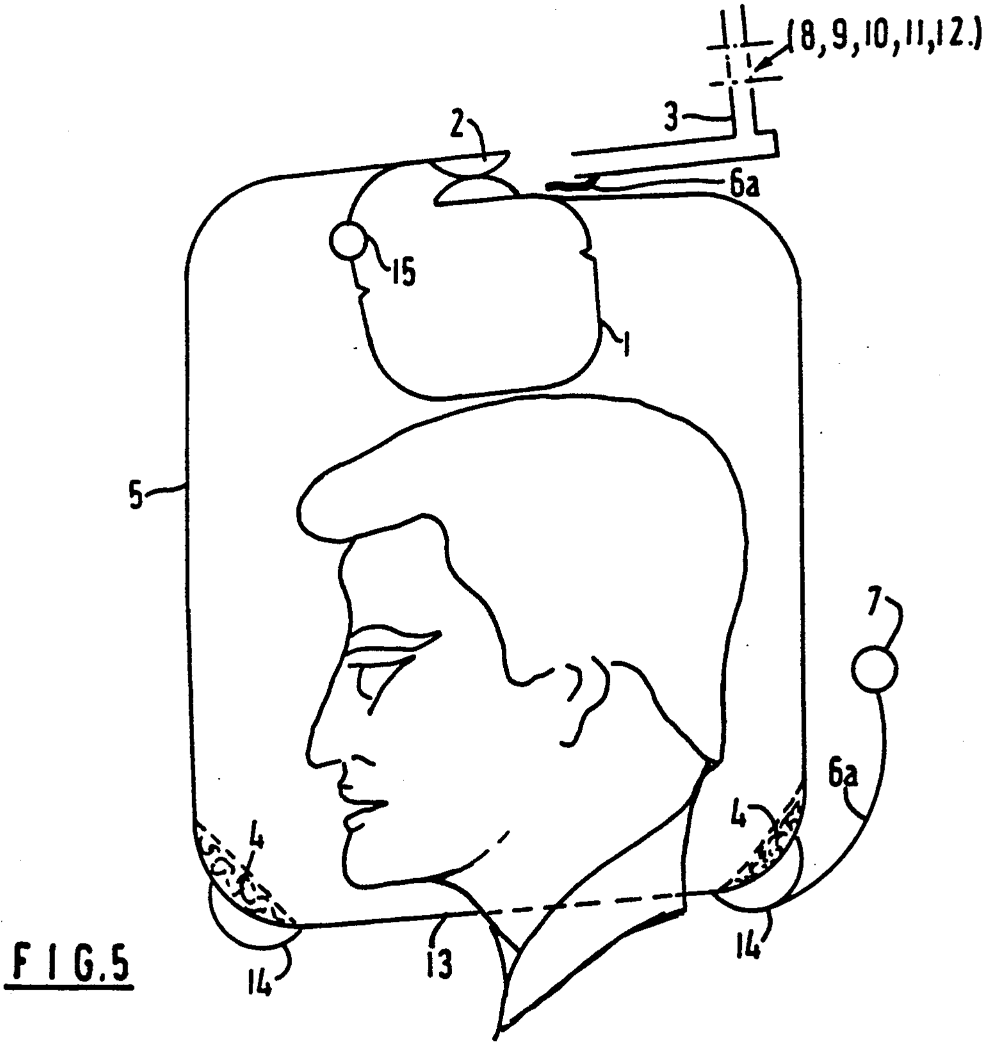
FIG. 5 schematically shows the face mask and hood arrangement of FIG. 4 in the operative position.

The oxygen supply system utilised in FIGS. 4 and 5 is that illustrated in FIG. 3. The face mask 1 is part of the wall of the hood at the dome, or possibly elsewhere, with the oxygen supply tube 3 at the apex. The dome is fixed to the face mask and the hood is folded like a concertina with a neck seal 13 fitted round the face mask to keep the hood interior sealed and therefore to keep the carbon dioxide absorber 4, which is spread out on the inside of the hood, switched out of the circuit. When used as an oxygen supply system for decompression or, as an air supply system for in flight fires, the face mask 1 is used. Additional valves may be provided to prevent back flow or to allow voiding to the external atmosphere and a collecting bag may also be provided. For escape, the hood is pulled over the head, using the handles 14 provided, and the oxygen supply tube 3 is pulled out. A release means 6A, attached to the tube 3 and to an integral oxygen cylinder 15 automatically switches on the oxygen supply from source 15. In a relatively large volume hood or envelope there is no separate rebreathing bag. The absorber is dispersed on and fixed to the inside surface of the hood. It is covered by a seal which is peeled back to expose the absorber when it is switched in to the circuit. However, it is important to have a smaller volume hood for airflow and a larger volume for escape when pure oxygen is used. For escape the oxygen source is activated at the same time as the absorber is switched in to the circuit. In a completely self contained system a separate oxygen supply and separate absorber might be used with a pure oxygen supply system for decompression. For in flight fires air flow is required with no absorber but it does not matter if an absorber is present provided that there is a sufficiently high air flow rate and that another absorber is available to be switched in for escape.

A securing means such a head harness or body harness, may be used to secure the face mask, hood or bag. The hood may be secured under a jacket or round the neck by an elastic grommet, that is polo neck or turtle neck, or by other means. The bag may be closed by a draw string or otherwise.

Additional eye protection means may be an eye shield or goggles with a face mask or may be transparent hood or bag or with a clear window or visor in it.

Other additions might include an ancillary portable oxygen or air supply, such as a small pressure cylinder which might also be activated by the same release means using a third cord. A separate release means could be used and would make the device more complex and difficult to use but this could be overcome by incorporating a time lapse switch to release the oxygen from the cylinder or a series of cylinders at fixed or presetable time intervals.

Figure 6:
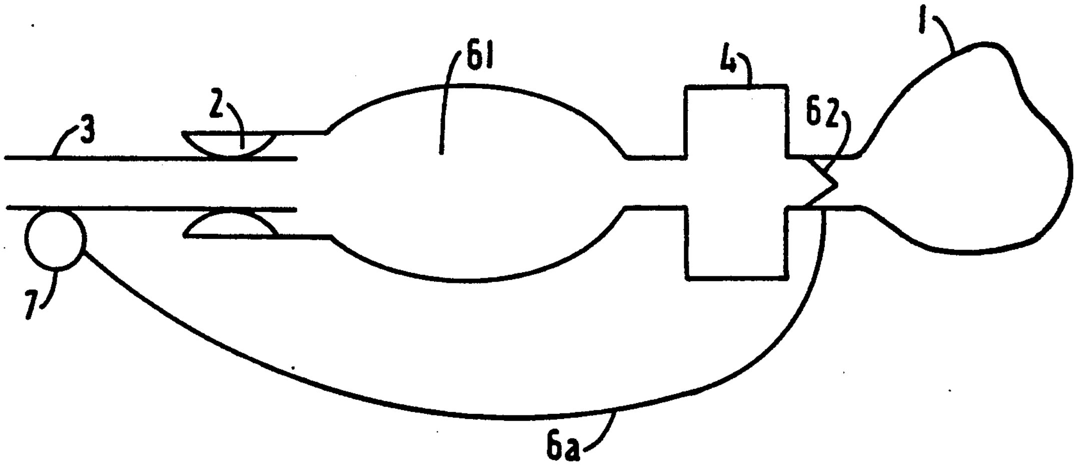
FIG. 6 schematically illustrates a modified system of the embodiment illustrated in FIGS. 1 and 2.
Figure 7:
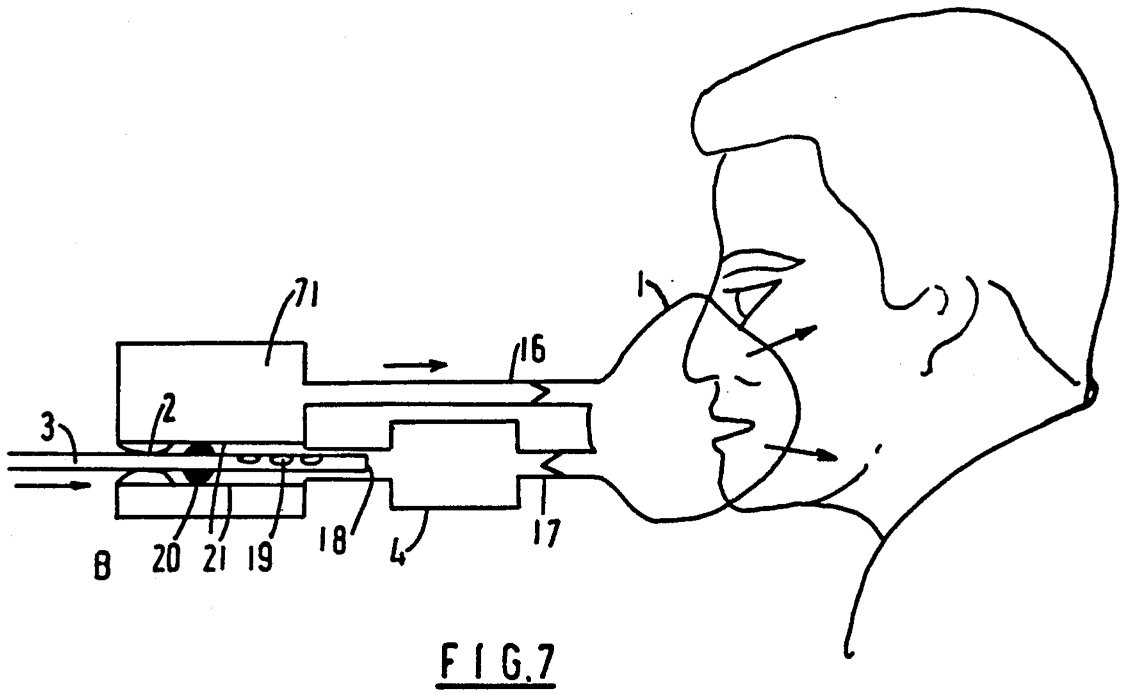
FIG. 7 diagrammatically illustrates a linear type arrangement of an embodiment in accordance with the invention.

A circulation means may comprise an additional system of one way valves and/or circuits to ensure passage of expired air through the absorption means. This additional system may be inside the mask or hood and may include a projection attached to one wall of the mask or hood to be an additional securing means when gripped by the teeth. The essence of the invention is means of switching the absorption means out of or in to the breathing circuit. This may be done in other ways so that the same reservoir may be used for rebreathing and for collecting. This system, shown for example in FIG. 6 consists of an arrangement in line of oxygen supply tube 3; self-closing valve 2, common reservoir 61,$CO_2$ absorber 4, additional valve 62 and face mask 1. The additional valve 62 allows gases to pass in to the face mask but not out. This system may be converted to a respirator if a release cord 6A attached to the guide ring 7 removes or holds open the valve 62 or opens a bypass which bypasses it. The bypass may for example be a collapsible rubber tube retained in a folded and closed condition by an elastic band attached by the cord and guide ring 7 to the supply tube 3. When the supply tube 3 is removed the elastic band is pulled off to release the bypass to the open condition. It will be appreciated by those skilled in the art that the diagrams illustrate principles which must be implemented in accordance with well established knowledge described for example in R. S. Atkins et al 1982, a synopsis of anaesthesia, Wright, Bristol. It will also be clear that the same result may be achieved in other ways. For example FIG. 7 shows in diagrammatic form a linear arrangement of oxygen supply tube 3, valve 2, dual purpose bag 71, absorber 4, and mask 1. One way valves with air flow direction indicated by arrows are placed in the mask inlet circuit 16 and in the rebreathing circuit 17 near the mask. The circuit 17 is occluded by an extension of the supply tube 18. Incoming air or oxygen enters the bag through holes 19 in the tube which has a fusiform enlargement 20 to prevent it slipping out. Expired air is vented to the cabin round the side of the mask. To facilitate reinsertion, a guide means 21 may be provided for example from metal rods fixed at each end. When, as in FIG. 8, the oxygen supply tube 3 is removed together with its extension 18, the rebreathing circuit 17 is no longer occluded. The apparatus is now a rebreathing system with gas flow from bag 71 by way of inlet circuit 16 to mask 1 and by way of rebreathing circuit 17 back to bag 71.

Figure 8:
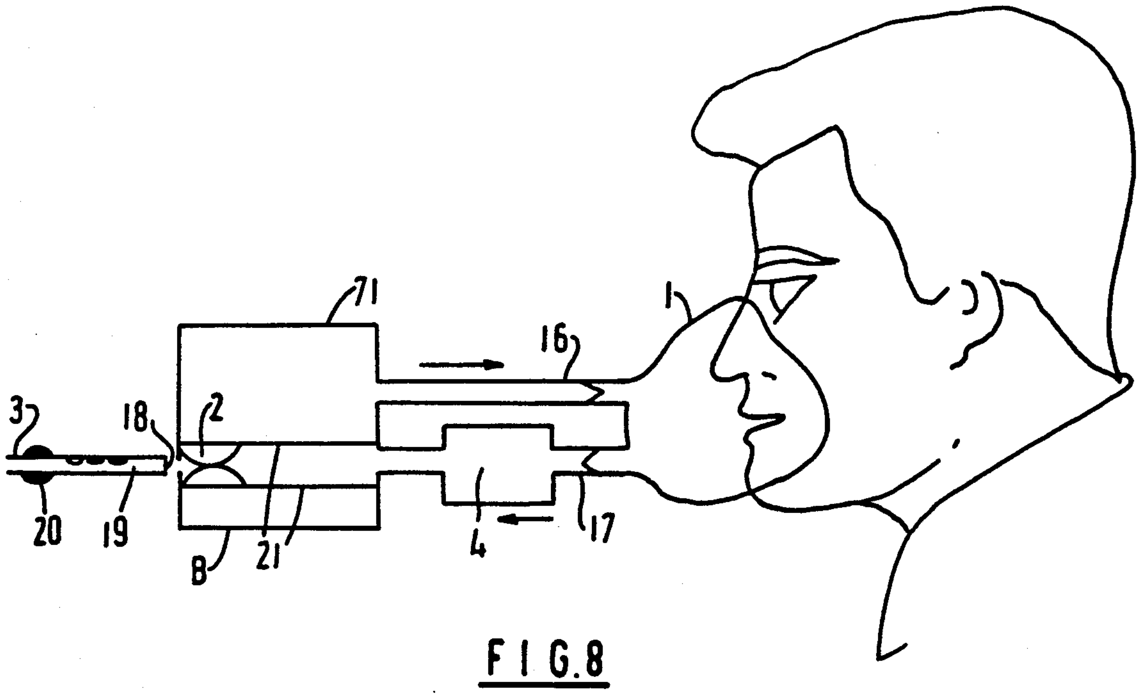
FIG. 8 diagrammatically illustrates the system of FIG. 7 but with the oxygen supply tube removed.

It is obvious to those skilled in the art that improvements may be made. For example the chamber 71 in FIGS. 7 and 8 may become a small junction chamber more simple to manufacture and the rebreathing bag may be connected to the surface B (FIG. 8). The inlet breathing circuit 16 and rebreathing circuit 17 may be concentric in cross section with the absorber 4 centrally placed so that the extension 18 may be conveniently inserted. Additional valves may be inserted and circuit 16 may be closed during rebreathing to ensure double passage of gases through absorber 4 during inspiration and expiration.

As previously mentioned the respiratory gases comprise oxygen either as pure oxygen or as air and the choice of gas would be made by the aircrew on the flight deck or by the cabin staff. An embodiment for automatic selection of gas or of gas mixture to conserve oxygen and in particular that stored under pressure for such pressurised oxygen is itself a fire hazard if the delivery or storage system is penetrated by the fire described with reference to FIG. 9. An electronic circuit is shown containing logic gates which are well known in the art. A logic gate having the function OR gives an output signal when there is an input signal in one input line OR in any other input line from a plurality of such inputs. A logic gate having the function AND gives an output signal when there is an input signal in one input line AND in all other input lines from a plurality of such inputs. A logic gate having the function NOT changes the signal state of input and output. Thus, there is NOT an output signal when there is an input signal and vice versa.

Figure 9:
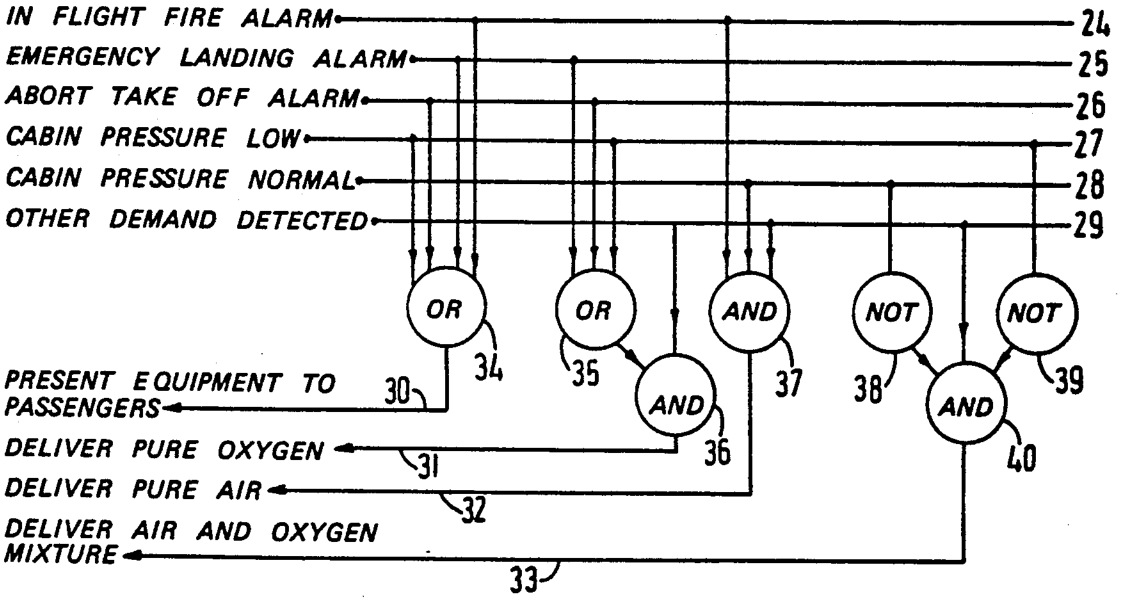
FIG. 9 is an electronic circuit for use in accordance with the present invention.

An embodiment of the logic circuit required for automatic delivery of apparatus and respiratory gases to aircraft passengers is shown in FIG. 9. It is well known in the art that additional devices all well known in the art are required for operation of said logic circuit. The plurality of additions not shown in the diagram include a power supply means, circuit closing means, for example a manually operated switch, and signal generating means. All input circuits 24–29 are connected to a plurality of alarm switches or detectors each of which generates a signal in the appropriate input circuits when operated manually or automatically to give warning of in flight condition. Such warning might include an indicator means, visual or auditory or other, to indicate that the receptacle means has been opened and thus detect, in an emergency, that all passengers are using, or attempting to use, breathing apparatus and, in the absence of an emergency, that someone is tampering with passenger protection apparatus. Such manual switches are distributed at convenient sites in the aircraft to be operated by flight deck or cabin staff. Such automatic detectors are also conveniently distributed for exercise of detection function. All output circuits 30–33 are connected to mechanical or electrical devices, whether valves or otherwise, to present breathing apparatus to passengers and to deliver in said oxygen supply tube appropriate gases or mixture of gases. The logical control decisions are made by logic gates 34–40 having inputs from input circuits and/or other logic gates and having outputs connected to other logic gates and/or output circuits. Warning of an in-flight fire is given manually by pressure on switch or automatically by smoke detection means or otherwise to generate a signal in circuit 24. Warning of emergency or precautionary landing is given by similar manual switch or otherwise to generate a signal in circuit 25. Warning of abort of take off similarly gives a signal in circuit 26. Cabin pressure may be detected by pressure sensors in the cabin or otherwise and a signal is generated in circuit 27 when said pressure is low and in circuit 28 when said pressure is normal. Outlet demand may be detected by breaking of a circuit when the box is opened or by pressure detectors in oxygen supply tube, compared if necessary with cabin pressure, to detect lowered pressure resulting from inspiration or otherwise and a signal is generated in circuit 29 when said demand is detected. The purpose of supply, only on demand, is to reduce loss of oxygen which may fuel a fire. The OR gate 34 has four inputs connected to circulate 24, 25, 26 and 27 and an output to secure release of breathing apparatus to passengers in any of the events recognised in said circuits 24 to 27. The OR gate 35 has three inputs connected to circuits 25, 26 and 27 and an output to AND gate 36. This has a corresponding input, an other input from circuit 29 and an output 31 to secure delivery of pure oxygen to passengers in the event of outlet demand AND one of the events signalled on circuits 25 to 27. The AND gate 37 has three inputs connected to circuits 24, 28 and 29 and output 32 is given to secure delivery of pure air to passengers. The AND gate 40 has an input from the output of NOT gate 36 the input of which is connected to circuit 28 such that AND gate 40 receives an input signal if input circuit 28 is NOT indicative of normal cabin pressure. A similar circuit through NOT gate 39 to input circuit 17 is such that AND gate 40 receives an input signal if input circuit 27 is not indicative of low cabin pressure. The third input to AND gate 40 is connected to the input circuit 29. Thus the output circuit 33 is activated if there is a signal on all three inputs of gate 40 to secure delivery of a mixture of oxygen and air.

It is obvious to those skilled in the art that another type of logic gate, for example NAND and NOR, may be used and that other types of device, for example fluid logic devices, may be used. It is also obvious that different pressure ranges, other than normal or low, may be recognised and that the proportion of air and oxygen may be adjusted accordingly, that is regulation of gases both in respect of quantity and quality. It is also obvious that detection of an excessive demand may indicate penetration of a supply line by fire with loss of gas and that in such event the corresponding supply sources should be shut off. It is also obvious to those skilled in the art that other devices such as microprocessors may be used and have advantages including ease of handling a multiplicity of signals, ability to deal with complexity and ease of re-programming in the light of experience.

Figure 10:
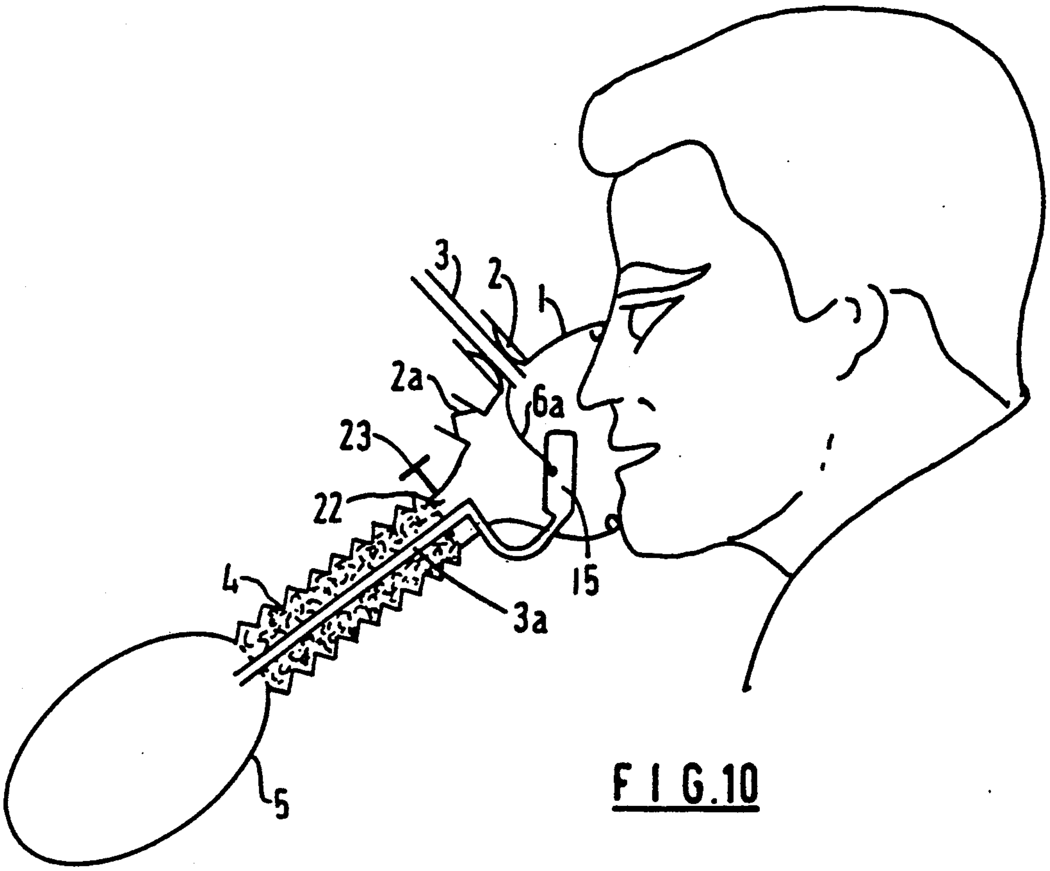
FIG. 10 is a schematic view of an alternative embodiment in accordance with the invention utilising a proximal seal assembly, coaxial oxygen supply tube and carbon dioxide absorber.

Referring to FIG. 10 the modified breathing apparatus comprises face mask 1, self closing valve 2, exit valve 2A, oxygen supply tube 3, carbon dioxide absorber 4, inflatable reservoir 5, oxygen source 15, seal assembly 22 handle and indicator 23 and oxygen delivery tube 3A. A release cord 6A is associated with oxygen source 15 to automatically commence operation thereof when the oxygen supply pipe 3 is pulled out of valve 2. It should be noted that exit valve 2A is in an alternative position to exit valve 12 in FIG. 3. Furthermore, as has been noted, valve 2 may be an exit valve.

The seal assembly may be operated to permit the rebreathing cycle to be entered. The device is held firmly against the apparatus container wall. In such arrangement, it is clear that the auxilliary device is not brought into operation. When the device has been removed from the apparatus container wall the indicator 23 is allowed to move and a free passage of oxygen is possible between mask 1 and reservoir 5.

The seal mechanism includes an obturator and a number of channels. When the oxygen is switched on the pressure of the oxygen pushes the obturator along until the opening is in line with the channels to the reservoir and mask. The end of the container wall prevents further movement. At this point, the end nearest to the oxygen source has moved beyond the oxygen supply tube and oxygen flows down this to the reservoir. The seals prevent leakage of oxygen or movement of gases except where intended.

In FIG. 10 the exit valve 2A is an alternative to 12 in FIG. 3. It should have an adjustable pressure setting with resistance set to be higher than the maximum pressure required for rebreathing but low enough to allow voiding to external atmosphere, when the system is full, to prevent lung damage from too high pressure due, for example, from malfunction of pressurised oxygen supply source.

Figure 11:
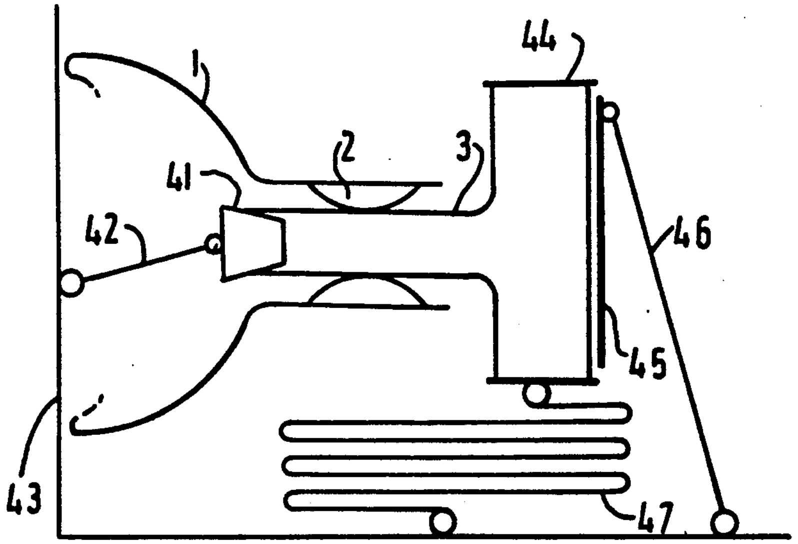
FIG. 11 diagrammatically illustrates a complete filter assembly and receptacle means which may be utilised in association with the device of the present invention.

As previously mentioned the respiratory gases comprise oxygen either as pure oxygen or as air and the choice of gas would be made by aircrew in the flight deck or by cabin staff. It should now be made clear that an alternative oxygen supply source includes pure oxygen from a chemical generator or stored oxygen and it also includes oxygen in air. Furthermore the air supply source may be ram air or bleed air or compressed air or filtered air. Filtered air will not protect against hot gases but filters can provide substantial protection until exhausted, until the air becomes too hot to breathe or until it is time to escape. However, a filter system with a heat sink added, may provide adequate protection against hot gases and may be preferred if it has other advantages, for example lightness of weight. A 500 gram filter may, depending upon smoke density and other factors, provide protection for 20 to 30 minutes and may be suitable for some in flight fires. It is an advantage that filters may be fitted without major engineering alterations to the aircraft. Additionally the filter should, like the carbon dioxide absorber, be sealed and a method of doing this is illustrated in FIG. 11. The cover 1 has a said self closing valve 2 and oxygen supply tube 3 passes therethrough. The proximal end of said oxygen supply tube 3 is sealed by a proximal seal means 41 attached by a proximal cord means 42 to a receptacle means 43 or box or otherwise fixed to the aircraft. The distal end of said oxygen supply tube 3 is connected to or becomes the proximal end of a filter means 44 and a distal seal means 45 seals the distal or air intake end of the filter and is connected by the distal cord means 46 to the receptacle means 43 or otherwise fixed. Thus removal of the mask and filter from the box automatically unseals the filter 44 and proximal end of said oxygen supply tube 3, by removing the seals 41 and 45. The filter 44 is also fixed to the receptacle means 43 by an additional cord means 47. This allows the filtered air system to be used by a seated passenger but it automatically separates the filter 44 and oxygen supply tube 3 from the cover 1 and self closing valve 2 when the passenger leaves his seat to escape from the aircraft. The said third cord to activate the stored oxygen source may also be attached to said filter 44 to ensure that said source is activated automatically at the time of escape. The said filter must be capable of removing smoke particles, carbon monoxide gas, cyanide gas and other toxic substances. The combination of a filtered air source with a pure oxygen rebreathing system may be described as a hybrid system. The device of FIG. 11 also includes, but not shown, an exit valve and a release mechanism to bring the rebreathing bag into operation.

The functions of the component parts of the apparatus are as follows.

The cover, the self-closing valve and the oxygen supply tube are as previously described.

The proximal seal means seals the proximal end of the oxygen supply tube.

The proximal cord means attaches the proximal seal means to the receptacle means.

The receptacle means holds the apparatus and is itself firmly fixed to the aircraft.

The filter means is the distal part of the oxygen supply tube and contains substances which remove by filtration noxious gases.

The distal seal means seals the distal or air intake end of the filter means.

The distal cord means attaches the distal seal means to the receptacle means.

The additional cord means attaches the filter means to the receptacle means and the cord is long enough for the apparatus to be removed from the box and used by a seated passenger.

The filter may be remote and may serve several passengers. It may have a long connecting tube (not short as shown) which may have an exit valve 12 as in FIG. 4 and/or collecting bag 9 and non-return valve 10. Such might be used with a motorised filter system.

Figure 12:
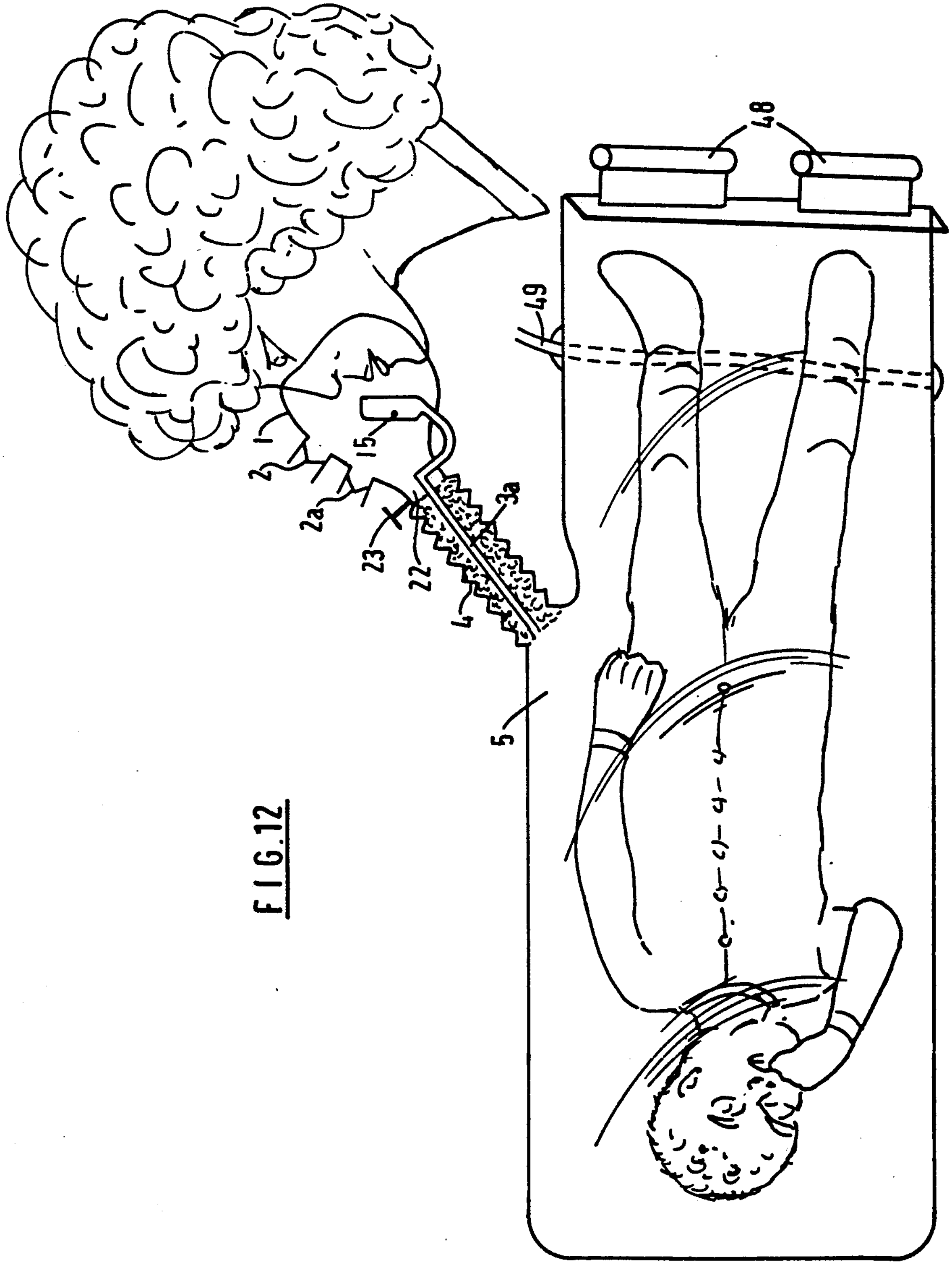
FIG. 12 shows a mother and baby unit.

The modified reservoir in the mother and baby unit (FIG. 12) is closed by folding over the end and holding it closed with spring clips 48, and in the mother and young child unit it is closed by a drawstring 49 round the abdomen.

Figure 13:
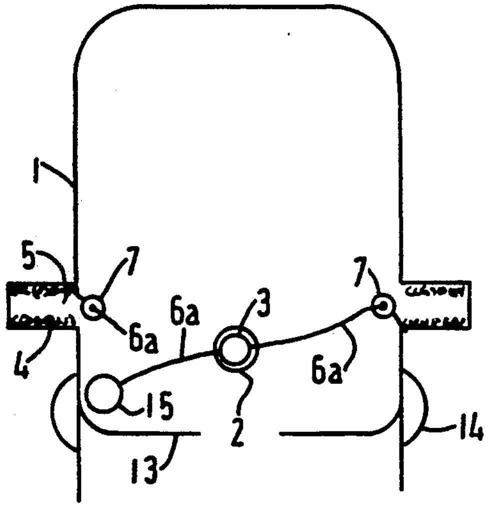
FIG. 13 diagrammatically illustrates a hood arrangement in the inoperative position.

In the sealed mode of a hood embodiment as shown in FIG. 13, the self closing valve 2 and oxygen supply tube 3 are connected to the cover means 1, which in turn is connected to the hood.

The hood is folded in the horizontal plane so that the absorber 4 is in a fold and the reservoir 5 is empty. The fold is kept in position by a series of radially positioned guide means 7 and by two release means 6A. An additional release means is required to activate the oxygen supply source 15. Each ring of the guide means is in a vertical plane with alternate rings attached to upper and lower edges of the fold. Each release means is attached at one end to the oxygen supply tube 3 and is threaded through the ipsilateral set of rings to keep the absorber 4 switched out of contact with the inspired and expired gases.

Figure 14:
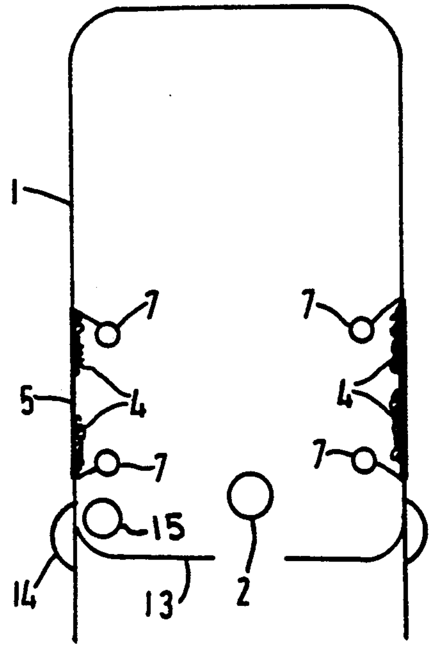
FIG. 14 diagrammaticaly illustrates the hood arrangement of FIG. 13 in the operative position.

The absorber is shown in FIG. 14 in the open circuit state. To switch the absorber in to the circuit the oxygen supply tube 3 is withdrawn and automatically pulls out both release means 6A. The opposed surfaces of the absorber 4 are no longer held together by the guide means 7 and the fold is unfolded by the pressure of oxygen to expose the absorber 4 in the cover means 1 and reservoir 5 which are now combined as one enlarged hood. A separate release means may be provided to switch in the absorber without pulling out the oxygen supply tube 3.

It is obvious to those skilled in the art that the fold in the hood may, alternatively or additionally, be in a vertical plane, coronal, sagital or other. A coronal fold would not obstruct vision and any vertical fold would decrease hood volume. Also the dome may be silvered to reflect heat. The oxygen supply tube 3, shown as sited low down, may be sited in the dome or elsewhere and the diagram is shown by way of example only. As in the face mask model one or more portable oxygen supply sources may be attached to the hood, for example a first pure oxygen source and a first absorber for decompression, a high flow air supply source for in flight fire and a second pure oxygen source and second absorber for escape.

Figure 15:
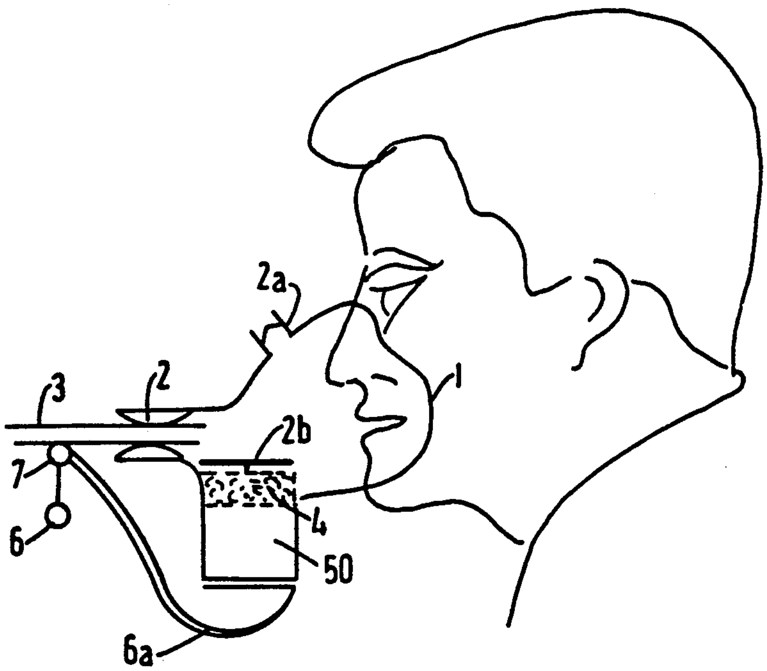
FIG. 15 diagrammatically illustrates a modification of the apparatus of FIG. 1 in which the reservoir is replaced by a filter.

The embodiment of FIG. 15 is similar to that of FIG. 1, but in which the reservoir 5 has been replaced by a filter 50.

The release means 6 and 6A unseal the filter 50 (in the manner as shown in FIG. 11). In this embodiment, an exit valve 2A is shown and there are two entrance valves. The first valve 2B is adjacent the carbon dioxide absorber 4 and the second valve is in the oxygen supply tube 3 (as previously described in FIG. 3 as valve 10). It should be noted that the opening pressures of valves 2B and 10 should be balanced such that valve 10 opens first and valve 2B does not open until no further gas can be obtained through valve 10, or through oxygen supply tube 3 at the site of valve 10; thus valve 2B will automatically open to supplement breathable gas when required if manual release 6 has been activated. The filter seal is required for the purpose of excluding air from the filter 50 during the storage mode.

It will be apparent to those skilled in the art that changes may be made in the shape, design and material composition of the apparatus and that a variety of manufacture methods, of types, of sizes and of devices may be used for the components thereof; face mask, oxygen supply tube, self closing valve, carbon dioxide absorber, retain/release mechanism, guide means and inflatable rebreathing bag reservoir. It will also be apparent to those skilled in the art that additional or ancilliary apparatus may be used including means of ensuring a well fitting face mask, including a head harness to hold the face mask in position, including goggles to protect the eyes from noxious gases and very hot air, and including an additional system of one way valves and/or circuits to ensure circulation, to or fro, of air from lungs to absorber, to reservoir and back to lungs. It will also be obvious to those skilled in the art that the apparatus illustrated, the methods suggested and the possibility for ancilliary apparatus are given by way of example only and do not exlude the many other methods or possibilities which are obvious for such breathing apparatus or ancilliary apparatus.

One further example may be given because of its simplicity and suitability for children of different sizes and ages and particularly for young children. In essence it is a large clear plastic bag connected to the oxygen supply tube through a self closing valve. The bag is placed over the head and shoulders and a seal is provided by putting on a pullover, anorak or jacket fastened up to the neck on top of the bag. The bag is inflated with oxygen and the oxygen and the oxygen supply tube is removed just before the child walks or is carried from the cabin of the aircraft. It will be appreciated that the principle is the same but the entire head is inside the rebreathing bag and a carbon dioxide absorber may not be necessary due to the relatively large volume of the microenvironment compared with the lung volume and the relatively short time for which it is required. Alternatively a young infant could be placed entirely inside the bag which could be closed at the distal end opposite to the oxygen outlet. However, it is safer to have an oxygen supply and carbon dioxide absorber as shown in the mother and baby unit.

The absorption of carbon dioxide is an exothermic reaction and it is obvious that it may be necessary to cool the gas coming out of the absorber or to disperse the heat or both. Cooling may be performed by chemical, physical or other means, for example by combining it with an endothermic reaction. Dispersion may be achieved by using a heat sink, for example contact with copper mesh or other good heat conductor, or by a circuit arrangement, for example single pass through the absorber from lungs to reservoir and return of mixed gases which bypass the absorber.

The body is an efficient heat sink because the latent heat of vapourisation of water is high and expired air contains much water vapour. It is obvious that removal of water vapour by a hygroscopic or deliquescent agent or otherwise will ensure the continued efficiency of this heat sink mechanism.

In any aircraft system weight is of paramount importance and if, for example, a filter system with a heat sink is found to provide adequate protection against hot gases but is lighter than, for example, a closed rebreathing system then this would be preferred.

Breathing apparatus may best be stored overhead and presented to passengers when required but this requires engineering modifications to aircraft. In the meantime, for apparatus fitted in to a seat back, an indication may be given when the container is opened. This will alert cabin staff to unauthorised use by children or others tampering, pilfering or attempting to don hoods for other than emergency use. For example a circuit may be broken when a lid is lifted and an indication given at a crew station.

The rebreathing bag may be the floatation chamber of a life jacket so that both life support systems, smoke protection and floatation, are combined.

It will also be apparent to those skilled in the art that such apparatus may be used in an industrial environment and in hotel, shop, office and house fires and may be used by firemen, miners, sewage workers, civilians and others and that additional or ancilliary apparatus may be used including means whether automatic or otherwise of delivering the apparatus to passengers when needed, including means of issuing instructions during the emergency, whether by automatic recorded message or otherwise, including indicator means, including means of inflating the reservoir directly from a fixed oxygen supply and including adaptation for use with closed oxygen or air supply systems as well as closed rebreathing systems. It will be obvious to those skilled in the art that the apparatus illustrated, the methods suggested and the possibility for ancillary apparatus are given by way of example only and do not exclude the many other methods or possibilities which are obvious for such breathing apparatus or ancilliary apparatus.

Of the many obvious places for use of such breathing apparatus hotels and multi-storey buildings for offices and shops or stores should be mentioned. Very similar apparatus could be kept in each room with a plurality of outlets from an oxygen cylinder supplying several rooms or a complete floor. Fire alarms could be linked to recorded instructions for using the apparatus. If the apparatus is removed from its storage place an electrical signal could be automatically transmitted to reception to indicate which items were being utilised. In hotel fires a longer time might be needed to escape and ancilliary apparatus such as oxygen sparklet or several such activated automatically at set time intervals or manually might be useful. Such apparatus might also be useful in industry in hostile environments to comply with Section 30 of the Factories Act 1961 and in mines and sewers where methane may collect. It is also obvious that the apparatus may be used in converse sequence that is conversion from portable breathing apparatus, used for example in rescuing people from house or hotel fires or mines or sewers, to an oxygen supply system, when the same apparatus is connected to a static oxygen source, once the victim has been removed from the hostile environment. The addition of a small portable oxygen source would be particularly suitable for this use. The apparatus may be used by firemen and by members of the armed forces during fires in aircraft, ships or buildings and by others. It will also be obvious that in the case of the armed forces the conversion may be from portable gas mask using filtration means to portable respirator using rebreathing bag with microenvironment and with further conversion option to static supply system.

It is, of course, possible to utilise the rebreathing system as the first oxygen supply system in the case of decompression and/or in flight fire and to switch to the filter system for escape from the aircraft.

I claim:

1. A breathing apparatus for persons, including aircraft passengers, said apparatus being operable in a first breathing mode to receive respiratory gasses from a first respiratory gas source and in a second breathing mode to receive respiratory gasses from a second respiratory gas source, comprising:

(a) conveyance means for conveying respiratory gasses to and from a person;

(b) first supply means for supplying respiratory gasses to said conveyance means from said first respiratory gas source the first supply means forming part of a first breathing circuit;

(c) second supply means for supplying respiratory gasses to said conveyance means from said second respiratory gas source, the second supply means forming part of a second breathing circuit;

(d) conversion means for automatically converting the mode of operation of the apparatus, upon activation, from said first breathing mode to said second breathing mode by cutting-off supply of respiratory gasses from said first supply means to said conveyance means while permitting supply of respiratory gasses from said second supply means to said conveyance means;

(e) carbon dioxide absorption means for absorbing carbon dioxide in said second breathing circuit after conversion of said mode of operation to said second breathing mode by said conversion means.

2. A breathing apparatus as claimed in claim 1, wherein said automatic conversion means comprises:

valve means detachably connected to said first supply means and which close to automatically prevent admission of undesired gasses into said conveyance means upon detachment of said first supply means from said valve means;

release means for permitting supply of respiratory gasses to said conveyance means from said second supply means; and guide means connected to said release means and to said first supply means to ensure activation of said release means on detachment of said first supply means from said valve means.

3. A breathing apparatus as claimed in 2, wherein said guide means is also arranged to activate said release means for permitting supply of respiratory gasses to said conveyance means from said second supply means without immediately initiating detachment of said first supply means from said valve means, said second supply means thereby supplementing the supply of respiratory gasses from said first supply means prior to said detachment and serving as the sole supply of respiratory gasses to said conveyance means after said detachment.

4. A breathing apparatus as claimed in claim 2, wherein said guide means first permits the supply of respiratory gasses to said conveyance means from said second supply means when said valve means closes to automatically prevent admission of undesired gasses into said conveyance means in response to detachment of said first supply means.

5. A breathing apparatus as claimed in claim 1, wherein said first respiratory gas source is activated when said breathing apparatus is removed from a storage site.

6. A breathing apparatus as claimed in claim 5, wherein said second respiratory gas source is activated when said conversion means is activated.

7. A breathing apparatus as claimed in claim 1, wherein all parts of said breathing apparatus are portable.

8. A breathing apparatus as claimed in claim 7, wherein said conversion means is activated when said first respiratory gas source is exhausted.

9. A breathing apparatus as claimed in claim 1, wherein said first breathing circuit is an open circuit from which exhaled gasses are voided to the environment.

10. A breathing apparatus as claimed in claim 1, wherein said first breathing circuit is a closed circuit in which exhaled gasses are retained, at least partially, within said closed circuit.

11. A breathing apparatus as claimed in claim 1, wherein said second breathing circuit is an open circuit from which exhaled gasses are voided to the environment.

12. A breathing apparatus as claimed in claim 1, wherein said second breathing circuit is a closed circuit in which exhaled gasses are retained, at least partially, within said closed circuit.

13. A breathing apparatus as claimed in claims 9, 10, 11, or 12, wherein said carbon dioxide absorption means is arranged to absorb carbon dioxide in both said first and second breathing circuits.

14. A breathing apparatus as claimed in claim 9, wherein said first respiratory gas source is arranged to supply to said first supply means a gas selected from the group consisting essentially of pure oxygen, filtered air, and compressed air.

15. A breathing apparatus as claimed in claim 10, wherein said first respiratory gas source supplies to said first supply means a gas selected from the group consisting essentially of compressed pure oxygen, chemically generated pure oxygen, and chemically purified expired oxygen.

16. A breathing apparatus as claimed in claim 11, wherein said second respiratory gas source is arranged to supply to said second supply means a gas selected from the group consisting essentially of pure oxygen, filtered air, and compressed air.

17. A breathing apparatus as claimed in claim 12, wherein said second respiratory gas source is arranged to supply to said second supply means a gas selected from the group consisting essentially of compressed pure oxygen, chemically generated pure oxygen, and chemically purified expired oxygen.

18. A breathing apparatus as claimed in claim 10, wherein said closed circuit includes reservoir means for rebreathing.

19. A breathing apparatus as claimed in claim 12, wherein said closed circuit includes reservoir means for rebreathing.

20. A breathing apparatus as claimed in claims 18 or 19, wherein said reservoir means forms a baby bag.

21. A breathing apparatus as claimed in claims 18 or 19, wherein said reservoir means forms part of a mother and baby unit.

22. A breathing apparatus as claimed in claims 18 or 19, wherein said rebreathing means includes collector means for accumulating respiratory gasses in order to compensate for differences in flow rate between a respective respiratory gas source and the respiration of said person.

23. A breathing apparatus as claimed in claim 1, wherein said conveyance means is selected from the group consisting of a partial face mask, a complete face mask, a hood, and a bag.

24. A breathing apparatus as claimed in claim 1, further including logic control unit means for controlling automatic delivery of the apparatus, selection and supply of respiratory gasses, broadcasting of instructions to passengers and providing indication if the apparatus has been tampered with.

25. A breathing apparatus as claimed in claim 1, wherein said breathing apparatus includes both a pure oxygen source and a filtered air source in which a filter, a carbon dioxide absorber, an exit valve, and an inlet valve enable supply of filtered air from said filtered air source.

26. A breathing apparatus as claimed in claims 9, 10, 11, or 12, wherein said breathing apparatus is arranged to permit conversion of said mode of operation from said second breathing mode back to said first breathing mode.

* * * * *